United States Patent [19]

Lafon

[11] 4,177,290

[45] Dec. 4, 1979

[54] ACETAMIDE DERIVATIVES

[75] Inventor: Louis Lafon, Paris, France

[73] Assignee: Laboratoire L. Lafon, Maisons Alfort, France

[21] Appl. No.: 885,009

[22] Filed: Mar. 9, 1978

[30] Foreign Application Priority Data

Mar. 31, 1977 [GB] United Kingdom ............... 13579/77

[51] Int. Cl.² .................. A61K 31/165; C07C 103/22; C07C 103/82; C07C 103/76
[52] U.S. Cl. ............................. 424/324; 260/239 BF; 260/326.42; 260/340.5 R; 260/558 S; 260/559 T; 260/558 A; 424/250; 424/267; 424/244; 424/274; 424/282; 544/159; 544/168; 544/393; 544/396; 546/234; 546/235; 424/248.5; 424/248.54

[58] Field of Search ......... 260/558 S, 559 T, 340.5 R; 424/324

[56] References Cited

U.S. PATENT DOCUMENTS

| 3,993,683 | 11/1976 | Nickl et al. ................. 260/558 S X |
| 4,062,973 | 12/1977 | Nickl et al. ................. 260/558 S X |

OTHER PUBLICATIONS

Dahlbom et al., CA 43:5018i (1949).

*Primary Examiner*—Thomas A. Waltz
*Attorney, Agent, or Firm*—Bacon & Thomas

[57] ABSTRACT

Novel acetamide derivatives have been discovered to have useful pharmaceutical activity on the central nervous system. They may be prepared by reacting the corresponding ester or acid halide with the appropriately substituted amine.

6 Claims, No Drawings

ACETAMIDE DERIVATIVES

The present invention relates to new acetamide derivatives, their preparation and their therapeutic compositions and uses, in particular as ingredients which are active on the central nervous system.

The new compounds according to the invention are acetamide derivatives of the general formula I:

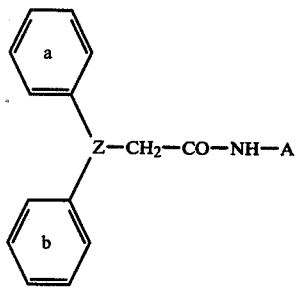

in which
each of rings a and b may optionally be substituted by one or more of the groups, F, Cl, Br, $CF_3$, $NO_2$, $NH_2$, $C_{1-4}$alkyl, $C_{1-4}$alkoxy and methylenedioxy;
Z is >CHSO— or >NCO—; and
A is hydrogen, $C_{1-4}$alkyl, $C_{1-4}$hydroxyalkyl or a group of the formula $R_1R_2N$—Y— in which Y is a divalent linear or branched chain $C_{1-4}$hydrocarbon radical, and either $R_1$ and $R_2$ are the same of different and are each hydrogen or $C_{1-4}$alkyl or $NR_1R_2$ is a heterocyclic group which has five to seven ring members including, optionally, a second heteroatom such as N or O, and which may be substituted; and the addition salts of the compounds wherein A is a basic group.

Among the groups which $NR_1R_2$ may represent, the following may be mentioned in particular: dimethylamino, diethylamino, pyrrolidino, piperidino, 4-methylpiperidino, 4-phenylpiperidino, 4-(p-chlorophenyl)-piperidino, morpholino, piperazino, 4-methylpiperazino, 4-(β-hydroxyethyl)piperazino, 4-phenylpiperazino, 4-(p-chlorophenyl)piperazino and perhydroazepino.

A is preferably hydrogen, β-hydroxymethyl or β-morpholinoethyl.

Particularly preferred compounds and salts of the invention are those of formula I in which neither of rings a and b is substituted, Z is as defined above and Y is hydrogen or β-morpholinoethyl.

Certain illustrative compounds of formula I in which rings (a) and (b) are unsubstituted are given in the following Table:

TABLE

| Code No. | Z | A | Melting point |
|---|---|---|---|
| CRL 40476 | >CH—SO— | H | 164–166° C. |
| CRL 40542 | >N—CO— | H | 136° C. |
| CRL 40543 | >N—CO— | β-morpholinoethyl | free base: 116–117° C.<br>HCl salt: 180–181° C. |

By addition salts there are understood here the acid addition salts of acids obtained by reacting the free base with a mineral or organic acid.

The compounds of formula I may be prepared by conventional methods. The preferred method of preparation comprises reacting an acid halide of formula II:

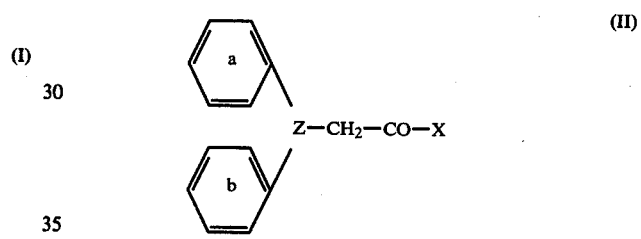

in which Z is as defined above, the rings (a) and (b) may be substituted as indicated above, and X is $C_{1-3}$alkoxy, F, Cl, Br or I, the preferred halogen being chlorine, with an amine of formula III:

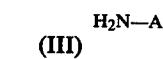

in which A is as defined above.

The sulphinyl compounds (Z=>CHSO—) are preferably prepared by the above method or by a variation of that method which comprises reacting a sulpho derivative of formula IIa:

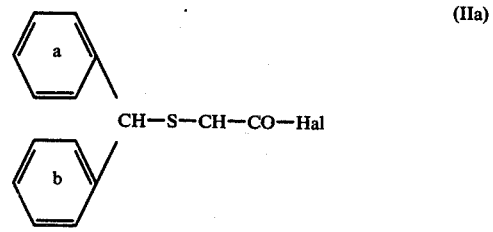

in which Hal is F, Cl, Br or I, preferably Cl, with an amine of formula III to obtain the corresponding sulphur amide which is oxidized with $H_2O_2$ to give the desired sulphinyl derivative.

A therapeutic composition according to the invention comprises a compound of formula I or one of its non-toxic addition salts in association with a physiologically acceptable excipient.

EXAMPLE 1

Benzhydrylsulphinylacetamide
$(C_6H_5)_2CH—SO—CH_2—CONH_2$

Code No.: CRL 40476

(1) Benzhydrylthioacetyl chloride 19.5 g (0.076 mol) of benzhydrylthioacetic acid in 114 ml of benzene are placed in a three-necked flask provided with a condenser and a dropping funnel. The mixture is heated and 19 ml of thionyl chloride are added drop by drop. Once the addition is complete, the reflux is continued for about 1 hour, cooling and filtering are carried out and the benzene and the excess thionyl chloride and then evaporated. In this way, a clear orange oil is obtained.

(2) Benzhydrylthioacetamide 35 ml of ammonia in 40 ml of water are introduced into a three-necked flask provided with a condenser and a dropping funnel and the benzhydrylthioacetyl chloride dissolved in about 100 ml of methylene chloride is added drop by drop. Once the addition is complete, the organic phase is washed with a dilute solution of soda and dried over $Na_2SO_4$, the solvent is evaporated and the residue is taken up in diisopropyl ether; in this way, the benzhydrylthioacetamide is crystallised. 16.8 g of product (yield = 86%) are obtained.

$M.p._{inst} = 110°$ C.

(3) CRL 40476

14.39 g (0.056) of benzhydrylthioacetamide are placed in a balloon flask and 60 ml of acetic acid and 5.6 ml of $H_2O_2$ (about 110 volumes) are added. The mixture is left in contact for one night at 40° C. and about 200 ml of water are then added; the CRL 40476 crystallises. By recrystallisation from methanol, 11.2 g of benzhydrylsulphinylacetamide are obtained.

Yield: 73%.

$M.p._{inst} = 164°-166°$ C.

EXAMPLE 1a

Example 1a relates to the same procedure for the manufacture of benzhydrylsulphinylacetamide (CRL 40476), as Example 1, but on an industrial scale.

(a) Benzhydrylthioacetic acid 1.003 kg of thiourea is dissolved in 5.72 liters of 48% hydrobromic acid and 0.880 liter of water in a 20-liter reaction vessel. The mixture is heated to 60° C. and 2.024 kg of benzhydrol are introduced. The temperature is increased to 95° C. and the contents of the vessel are allowed to cool to room temperature (15°-25° C.). The crystals are filtered off and washed with water. They are made into a paste again in 5.5 liters of water and this is introduced into a 20-liter reaction vessel with 3.5 liters of soda lye (d = 1.33). The mixture is heated to 70° C. and 1144 g of chloroacetic acid dissolved in 2.2 liters of water are passed in slowly. The reflux is maintained for 30 minutes after the chloroacetic acid has been passed in. The contents of the vessel are allowed to cool to room temperature (in this way, the benzhydrylthioacetic acid is obtained, but is not isolated).

(b) Benzhydrylsulphinylacetic acid 1.430 liters of hydrogen peroxide at 130 volumes are passed in over 3 hours at about 30° C. into the above reaction mixture. 22 liters of water are then passed in, the insoluble material is filtered off and acidification is carried out with hydrochloric acid (d = 1.18). Filtration, washing with water to reform a paste and drying without heat are carried out. In this way, the benzhydrylsulphinylacetic acid is obtained.

(c) Methyl benzhydrylsulphinylacetate

The above acid is placed in a 20-liter reaction vessel with 6 liters of water. 1.1 liters of soda lye (d = 1.33) and 1.848 kg of sodium bicarbonate are added. 2.1 liters of dimethyl sulphate are added. After one hour, crystallisation is induced. Filtration, drying without heat and washing are carried out. Methyl benzhydrylsulphinylacetate is obtained.

(d) CRL 40476

1 kg of methyl benzhydrylsulphinylacetate is dissolved in 3.5 liters of anhydrous methanol in a 10-liter balloon flask. $NH_3$ is bubbled in at a high rate of flow for 1 hour, and then left in contact for 4 hours. Filtration, drying without heat and washing with water are then carried out. By recrystallisation from a mixture of water and methanol (4:1 v/v) and then from a mixture of water and methanol (9:1 v/v) and drying under reduced pressure, CRL 40476 is obtained in the form of a white crystalline powder.

$M.p._{inst}$ (Köfler): 164°-166° C.

Total yield (calculated from the benzhydrol): 41%.

EXAMPLE 2

N,N-diphenylmalonamide
$(C_6H_5)_2—N—CO—CH_2—CONH_2$

Code No.: CRL 40542

N,N-diphenylchloroacetamide (M.p. = 117°-118° C.; yield: 89%) is prepared by reacting 34 g (0.2 mol) of diphenylamine with 11.3 g (0.1 mol) of chloroacetyl chloride in benzene. N,N-diphenylcarbamylacetonitrile (M.p. = 151°-152° C.; yield: 64%) is then prepared by reacting 24.55 g (0.1 mol) of N.N-diphenylchloroacetamide with 7.7 g (0.11 mol) of KCN in a mixture of methanol (300 ml) and water (100 ml).

18 g (0.075 mol) of N,N-diphenylcarbamylacetonitrile are subjected to hydrolysis for 24 hours at 20° C. in a mixture of concentrated $H_2SO_4$ (120 ml) and $H_2O$ (15 ml). The resulting solution is poured, with agitation, into 500 g of ice Drying without heat and washing with water and then with sodium bicarbonate are carried out; the crystals are dried and recrystallised in ethanol to obtain CRL 40542.

Yield 44%.

M.p. = 136° C.

EXAMPLE 3

N,N-diphenyl-N'-β-morpholinoethylmalonamide hydrochloride

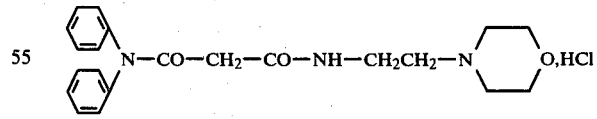

Code No.: CRL 40543

(1) N,N-diphenylcarbamoylacetic acid 22.6 g (0.08 mol) of ethyl N,N-diphenylcarbamoylacetate (m.p. = 75°-76° C.) are added to a solution of 5.6 g (0.1 mol) of KOH in a mixture of 50 ml of water and 25 ml of ethanol. The mixture is heated to 40° C. with agitation until dissolution is complete (that is, for about 1 hour) and agitation is continued for two hours. Acidification is then carried out with 3 N HCl, followed by drying without heat, washing with water and drying. 20.2 g (yield: 98%) of N,N-diphenylcarbamoylacetic acid (m.p.=126°-127° C.) are obtained.

(2) N,N-diphenyl-N'-β-morpholinoethylmalonamide

A solution of 13 g (0.05 mol) of N,N-diphenylcarbamoylacetic acid and 7.1 g (0.055 mol) of N-(2-aminoethyl)morpholine in 120 ml of methylene chloride is refluxed with agitation. A solution of 11 g (0.055 mol) of dicyclohexylcarbodiimide in 30 ml of $CH_2Cl_2$ is slowly added and the mixture is maintained under reflux for 3 hours.

After standing for one night, the dicyclohexylurea precipitate is filtered off, the filtrate is extracted with dilute HCl, the aqueous layer is decanted and it is made strongly alkaline with concentrated NaOH. Drying without heat, washing with water and drying are carried out; by recrystallisation from ethyl acetate, 16 g of the title base are obtained.

M.p.=166°-117° C.

(3) CRL 40543

The above base is solubilised in 300 ml of ethyl acetate and acidified with ethanol hydrochloride. The title hydrochloride precipitates and is recovered by drying without heat. By recrystallisation from ethanol, CRL 40543 is obtained.

Yield: 78%

M.p.=180°-181° C.

The results of the pharmacological tests which were undertaken with the compounds according to the invention and in particular the products of Examples 1 to 3 are summarised below.

In the following, in the absence of precise details to the contrary, each product was administered intraperitoneally in suspension in a gummy solution (gum arabic), in a volume of 20 ml/kg to mice and 5 ml/kg to rats.

TESTS WITH CRL 40476

I—TOXICITY

At a dose of 1024 mg/kg, the administration of CRL 40476 was followed by a decrease in motive activity, the gait being abnormal, by dyspnoea and by convulsions which appeared 40 minutes after injection; the animal was found dead after 24 hours. At a dose of 512 mg/kg, the symptoms were identical, but the animal survived. At 256 mg/kg hypermotility was noted above all, accompanied by sniffing, perhaps stereotyped, the gait was abnormal and the animal showed dyspnoea. At 128 and 64 mg/kg, the hypermotility and the stereotyped sniffing were still present for more than 3 hours. The maximum non-fatal dose per os was higher than 512 mg/kg.

II—INTERACTION WITH APOMORPHINE (1) Rats

Batches of 6 rats each received a subcutaneous injection of 0.5 mg/kg of apomorphine 30 minutes after the administration of CRL 40476. It was found that, with a strong dose, CRL 40476 seemed moderately to potentiate the stereotypy of apomorphine.

(2) Mice

Bathces of 6 mice received CRL 40476 30 minutes before the subcutaneous injection of 1 mg/kg of apomorphine. It was observed that CRL 40476 did not counteract the hypothermia, stereotypy and verticalisation behaviour induced in the mice by the apomorphine.

III—INTERACTION WITH AMPHETAMINE

Amphetamine (2 mg/kg) was injected intraperitoneally into batches of 6 rats 30 minutes after the administration of CRL 40476. It was found that CRL 40476 does not exert any effect with respect to amphetamine stereotypy.

IV—INTERACTION WITH RESERPINE

Batches of 6 mice received an intraperitoneal injection of reserpine (2.5 mg/kg) four hours before the administration of CRL 40476. In doses of 16, 64 and 256 mg/kg, CRL 40476 partially counteracted the body temperature lowering effects of the reserpine, but the reserpine ptosis was not changed by CRL 40476.

V—INTERACTION WITH OXOTREMORINE

Oxotremorine (0.5 mg/kg) was administered intraperitoneally to batches of 6 mice 30 minutes after the administration of CRL 40476. The hypothermia induced by the oxotremorine was not changed by CRL 40476; CRL 40476 was devoid of activity with respect to the trembling caused by the oxotremorine; and CRL 40476 did not alter the lacrymal and salivary hypersecretion and the defecation following upon the administration of oxotremorine.

VI—ACTION ON THE FOUR-PLAQUE TEST, TRACTION AND ELECTRIC SHOCK

The test was performed on batches of 10 mice 30 minutes after the administration of CRL 40476. It was noted that CRL 40476 led to an increase in the number of punished passages (probably in connection with an exciting effect), that it did not cause any major motor deficit, and that, in strong doses (from 64 to 256 mg/kg), it counteracted the convulsing effect of electric shock.

VII—ACTION ON SPONTANEOUS MOTILITY

Mice (12 per dose, 24 controls) received CRL 40476 at different times (15 minutes, 30 minutes, 1 hour, 2 hours, and 4 hours) before being placed in an actimeter (time 0); their mobility was recorded for 30 minutes. (1) Intraperitoneally, CRL 40476 leads to an increase in motility which is perceptible from 16 mg/kg. This effect begins rapidly (less than 15 minutes) and reaches its maximum 30 to 60 minutes after injection, then decreases, the duration of action being proportional to the doses.

(2) By the gastric route, at a dose of 64 mg/kg and above, CRL 40476 leads to considerable hypermotility commencing almost immediately after the injection and lasting for at least 2 hours. It is probable that, with a smaller dose (32 and 16 mg/kg), this effect is still present, but lasts less long.

(3) To determine the effect of repeated administrations, mice (12 per dose, 24 controls) received a daily intraperitoneal administration of distilled water or CRL 40476. On the fifth day, the animals were placed in the actimeters 30 minutes after the last administration and their motility was recorded for 30 minutes. CRL 40476 was found to retain its activity on the motility of the mouse; the activity was neither reduced nor increased with respect to the effect of a single injection.

VIII—ACTION ON INTERGROUP AGGRESSIVENESS

After a stay of 3 weeks in each of the halves of a box separated by an opaque partition, groups of three mice received CRL 40476. Half an hour later, they were brought together by withdrawing the partition and the number of fights that occurred in the course of 10 minutes was noted. It was observed that CRL 40476 did not exert any distinct effect on intergroup aggressiveness in mice.

IX—INTERACTION WITH HYPNOTICS (1) Batches of 10 mice received CRL 40476 30 minutes before the administration of a hypnogenic dose of chloral (400 mg/kg, injected intraperitoneally).

At a low dose (16 and 32 mg/kg), CRL 40476 reduced significantly the length of the sleep induced by the chloral. By increasing the doses, this effect disappeared, but the number of mice put to sleep decreased.

(2) Metaqualone (125 mg/kg) was injected intraperitoneally into batches of 10 mice 30 minutes after the administration of CRL 40476.

At a low dose, CRL 40476 did not alter the length of the sleep induced by the metaqualone, but by increasing the doses the number of mice put to sleep decreased, whereas the length of the sleep increased significantly. 30 With mice used for recording motility after repeated administrations of CRL 40476, pentobarbital (50 mg/kg, administered intraperitoneally) was injected into the mice as soon as the recording of spontaneous motility was completed, that is 60 minutes after the final administration of CRL 40476.

CRL 40476 did not alter the length of the barbiturate-induced sleep. With repeated administrations, it led to a reduction of the length of the sleep with respect to the effects of a single administration.

X—INTERACTION WITH YOHIMBINE

CRL 40476 was administered to mice grouped in fives one hour before the injection of a subtoxic dose of yohimbine hydrochloride (40 mg/kg, administered subcutaneously). The death rate was taken 24 hours later. It was found that CRL 40476 potentiated the toxicity of the yohimbine.

XI—INTERACTION WITH 5-HYDROXYTRYPTOPHAN and I.M.A.O.

Batches of 10 mice received a gastric administration of Nialamide (20 mg/kg) 18 hours before an intraperitoneal injection of DL-5-HTP. In doses of 32, 64 and 128 mg/kg, CRL 40476 did not lead to potentiation of the generalised trembling and head shaking. At 256 mg/kg, it caused an increase in the number of mice showing generalised trembling at the same time as a considerable death rate (30%) appeared.

XII—ACTION IN RELATION TO SOME BEHAVIOURAL CHARACTERISTICS DISTURBED BY VARIOUS AGENTS (1) Motility reduced by habituation After a sojourn of 18 hours, mice received CRL 40476. Immediately afterwards they returned to their respective enclosures and half an hour later the recording of motility began and was continued for 30 minutes. It was found that CRL 40476 caused, starting from a dose of 2 mg/kg, an appreciable resumption at a dose of 2 or 4 mg/kg. This effect was very marked at 8 and 16 mg/kg.

(2) Motility reduced by hypoxic aggression 30 minutes after receiving CRL 40476, mice were subjected to hypobaric anoxia (depression of 600 mm Hg in 90 s, expansion of 45 s), and they were then placed in an actimeter where their motility was recorded for 10 minutes. It was observed that, for doses higher than 16 mg/kg, CRL 40476 led to an improvement in motor recovery in mice whose motility has been lowered by hypoxic aggression.

(3) Asphyxic anoxia

Mice (10 per dose, 20 controls) received an intraperitoneal injection of gallamine triethiodide at a dose of 32 mg/kg 30 minutes after the administration of CRL 40476 and the time taken for the appearance of convulsions and death was noted. It was found that, in doses of 256, 128, 64 and 32 mg/kg, CRL 40476 did not lead to any increase in the time taken for the appearance of convulsions and death.

(4) Prolonged avoidance conditioning

Rats placed in a shuttle box were conditioned to avoid an electric shock (5 s) by changing compartments. The shock was preceded (3 s) by an acoustic and light signal appearing every 20 seconds. When the animals were perfectly conditioned, they remained subjected to the signal and possibly to the shock until apparent disappearance of conditioning, which generally occurred after 24 hours.

CRL 40476 was then administered intraperitoneally and the possible resumption of avoidance was reckoned until disappearance of the effect; at a dose of 128 mg/kg, CRL 40476 caused very distinct resumption of avoidance in the animals whose conditioning had apparently disappeared following a prolongation of the session. With a lower dose (64 mg/kg), this effect was practically non-existant.

XIII—CONCLUSIONS

CRL 40476 presents a neuropsychopharmacological spectrum characterised by the presence of excitation with hyperactivity and of hypermotility; and by the absence of stereotypy (except in strong doses) and of potentialisation of the effects of apomorphine and amphetamine.

Moreover, in some respects, CRL 40476 could approximate to the imipramine antidepressants (antagonism to reserpine hypothermia, potentation of the toxicity of yohimbine), but the absence of potentiation of 5-HTP and of antagonism to the hypothermia induced by apomorphine would make it a very special case in this pharmacological class.

Finally, in mice whose motility has been reduced by habituation of their enclosure, the presence of a motor stimulation with doses which do not cause hypermotility would seem to indicate a greater stimulation of psychism than of activity.

TESTS WITH CLR 40542 and CRL 40543

The following tests are numbered parallel to those for CRL 40476:

I. The LD-O of CRL 40542 is greater than 1024 mg/kg. and greater than 512 mg/kg for CRL 40543. At doses of 256 and 128 mg/kg, hyperactivity is observed for both products.

II. In rats, CRL 40542 potentiates the stereotypy of apomorphine but CRL 40543 does not affect the stereotyped behaviour induced by apomorphine. In mice, the two products (at doses of 1 and 16 mg/kg) do not modify the hypothermia and the stereotyped behaviour induced by the subcutaneous administration of apomorphine at doses of 1 and 16 mg/kg.

III. At a dose of 256 mg/kg, CRL 40542 potentiates, but CRL 40543 does not modify, the amphetamine stereotypy.

IV. The hypothermia induced by reserpine is antagonised by CRL 40542 at a dose of 128 mg/kg and aggravated at a dose of 512 mg/kg. CRL 40543 does not modify reserpine-induced hypothermia. Neither product has any action with respect to reserpine ptosis.

V. The hypothermia induced by oxotremorine is antagonised by CRL 40542 at doses of 32 and 128 mg/kg and by CRL 40543 at a dose of 256 mg/kg. Neither product is active on the trembling or peripheral cholinergic symptoms provoked by oxotremorine.

VI. CRL 40542 (at 32 and 128 mg/kg doses) and CRL 40543 (at 128 and 256 mg/kg doses) led to an increase in the number of punished passages. CRL 40542 (at 32, 128 and 512 mg/kg doses) counteracted the convulsive effect of electric shocks, but CRL 40543

(at 128 and 256 mg/kg doses) did not modify the convulsions.

VII. CRL 40542 does not appear to modify spontaneous motor activity. In mice, CRL 40543 leads to an increase in motor activity, at a dose of 256 mg/kg.

VIII. CRL 40542 does not provoke any noticeable change in intergroup aggression. CRL 40543, at a dose of 16 to 256 mg/kg, leads to a reduction in the number of fights.

XII. CRL 40542 (at a 8 mg/kg dose) and CRL 40543 (at 16 and 64 mg/kg doses) lead to a resumption of motor activity in mice whose motility has been reduced by staying in the same enclosure.

CRL 40542 (at 32, 64 and 128 mg/kg doses) and CRL 40543 (at a 256 mg/kg dose) lead to an ameloriation of motor recovery in mice whose motility has been reduced by hypoxic aggression.

With regard to asphyxic anoxia, CRL 40542 and CRL 40543 lead, with strong doses, to a shortening of the delay in the appearance of convulsions and death caused by gallamine triethiodate, a curarizing agent.

XIII. The neuropsychopharmacological study of CRL 40542 reveals a number of excitator behavioural effects; excitation with hyperactivity in mice and rats; the presence of stereotypy and the potentiation of the stereotyped effects owing to apomorphine and amphetamine; an increase in motility in animals whose activity has been reduced by habituation or hypoxic aggression; "anti-fatigue" activity in an avoidance conditioning test over a prolonged period; the presence of convulsions at high doses; and the moderate antagonism of hypothermia induced by oxotremorine or reserpine.

CRL 40543 shows a certain number of excitatory properties (excitation, hyperactivity and hypermotility) which can be accounted for in the results observed in the four plaque test. Further, the compound possesses convulsive activity which leads to heightening of convulsions induced by asphyxic anoxia. Finally, it exerts an anti-aggressive effect at all doses.

The compounds according to the invention are useful as therapeutic agents in the treatment of neurophysical disorders, being agents active on the central nervous system.

In man, CRL 40476 can be used in the form of capsules or compressed tablets at a dose of 200 mg, three times daily. Very favourable results are obtained in the treatment of aged asthenics. Further, without antagonisation of antipsychotic effects, the compound has proved to be useful in the treatment of slow dyskinesia in neuroleptics.

I claim:

1. An acetamide derivative selected from the compounds of formula I

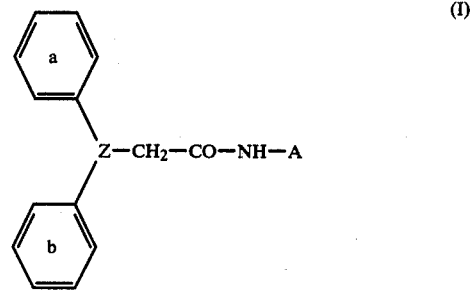

wherein ring a and ring b are each substituted zero, one or more times by substituents selected from the group consisting of fluoro, chloro, bromo, trifluoromethyl, nitro, amino, alkyl of 1 to 4 carbon atoms, inclusive, alkoxy of 1 to 4 carbon atoms, inclusive, and methylenedioxy; wherein Z is the radical >CHSO—; and wherein A is selected from the group consisting of hydrogen, alkyl of 1 to 4 carbon atoms, inclusive, hydroxyalkyl of 1 to 4 carbon atoms, inclusive, and a group of formula $R_1R_2N-Y-$ wherein Y is a divalent linear or branched chain hydrocarbon radical having 1 to 4 carbon atoms, inclusive, in the chain, and $R_1$ and $R_2$, being the same or different, are selected from the group consisting of hydrogen and alkyl of 1 to 4 carbon atoms, inclusive; and addition salts of the compounds wherein A is a basic group.

2. A compound of claim 1 wherein A is $R_1R_2N-Y-$ wherein Y is a divalent linear or branched chain hydrocarbon radical having 1 to 4 carbon atoms, inclusive, in the chain, and $R_1$ and $R_2$, together with the N atom to which they are attached, form a group selected from the group consisting of dimethylamine and diethylamine.

3. A compound of claim 1 wherein rings a and b are both unsubstituted and A is hydrogen, and pharmacologically acceptable acid addition salts thereof.

4. A compound of claim 1 which is benzhydrylsulphinylacetamide.

5. A pharmaceutical composition having activity on the central nervous system and consisting of, as an essential active ingredient, an active amount of a compound of claim 1.

6. The compound of claim 1, wherein Z is —CHSO— and A is hydrogen, alkyl of 1 to 4 carbon atoms or hydroxyalkyl of 1 to 4 carbon atoms.

* * * * *